(12) United States Patent
Nakatsu et al.

(10) Patent No.: US 6,849,240 B2
(45) Date of Patent: Feb. 1, 2005

(54) METHOD FOR IMPROVING THE DELIVERY OF VOLATILES FROM A BURNING CANDLE AND A SYSTEM FOR THE SAME

(75) Inventors: Tetsuo Nakatsu, Chappaqua, NY (US); Augustinus G. Van Loveren, Bedford, NY (US)

(73) Assignee: International Art and Science Group, Inc., Chappaqua, NY (US)

( * ) Notice: Subject to any disclaimer, the term of this patent is extended or adjusted under 35 U.S.C. 154(b) by 40 days.

(21) Appl. No.: 10/384,906

(22) Filed: Mar. 8, 2003

(65) Prior Publication Data

US 2004/0175287 A1 Sep. 9, 2004

(51) Int. Cl.⁷ .................................................. A62B 7/08
(52) U.S. Cl. ...................... 422/126; 422/120; 431/288; 431/289; 431/290; 431/291
(58) Field of Search ................................ 422/126, 120; 431/288, 289, 290, 291

(56) References Cited

U.S. PATENT DOCUMENTS

| | | | | |
|---|---|---|---|---|
| 4,184,195 A | * | 1/1980 | Duncan | 362/163 |
| 4,524,408 A | * | 6/1985 | Minera | 362/163 |
| 5,197,454 A | | 3/1993 | Lee | 126/9 |
| 6,152,728 A | | 11/2000 | Griffel | 431/293 |
| 6,190,439 B1 | | 2/2001 | Bresnahan et al. | 95/273 |
| 6,354,710 B1 | | 3/2002 | Nacouzi | 362/96 |

OTHER PUBLICATIONS

International Search Report for PCT/US04/06964 (applicant's PCT application), 6 pages including preliminary opinion, dated Oct. 6, 2004.

* cited by examiner

Primary Examiner—Krisanne Jastrzab
(74) Attorney, Agent, or Firm—Andrew F. Young, P.C.

(57) ABSTRACT

The invention provides a system and a method for improving the delivery of volatiles from a burning candle by providing a stabilized laminar gas flow adjacent a volatile-containing molten pool, ensuring an enlarged molten pool by close regulation of thermal transfer between a monolithic candle mass and the surrounding atmosphere, and minimizing volatile loss through unregulated thermal gradients.

19 Claims, 8 Drawing Sheets

Fig. 1

PRIOR ART

METHOD FOR IMPROVING THE DELIVERY OF VOLATILES FROM A BURNING CANDLE AND A SYSTEM FOR THE SAME

BACKGROUND OF THE INVENTION

1. Field of the Invention

The present invention relates to a method and an apparatus for improving and regulating the delivery of volatiles from a burning candle. More specifically, the present invention relates to a system used to improve the delivery of volatiles from a burning candle while both minimizing volatile loss through thermal breakdown and increasing or controlling a molten pool size 2. Description of the Related Art Fragrances, aromas, pesticides, and even anti-microbial compounds are commonly dispersed, into the atmosphere for a wide variety of reasons. Fragrances and aromas are used to improve the 'feel' or 'mood' of a location, and are often used to either improve an original emotional response or aid in the development of a specific emotional response. To these ends, fragrances and aromas are used in retail spaces to improve and focus customer sales, in emotional therapy ('aromatherapy') to soothe the psyche, in work places to invigorate the mind, and in medical therapy to soothe both the practitioner and the patient while improving healing rates in a stressful environment.

Pesticides and pest repellants are used to either remove or displace unwanted insects from a particular local. Pesticides are used in commercial, retail, and hospital environments to prevent insect damage and maintain property values. Pest repellants are also commonly employed in commercial, medical, and residential cleaning to prevent pest encroachment and provide an enjoyable environment in which to work, play, or rest.

Anti-microbial compounds are most commonly used to remove or destroy health-damaging microbes in hospitals and medical facilities, but may also be used in group retirement homes or individual residences to minimize disease transfer and improve health.

In sum, fragrances, aromas, essential oils, pesticides, insecticides, pest-repellents, and even the anti-microbial compounds noted above, while containing markedly different compounds with differing molecular weights, may be conveniently referred to as volatiles. These volatiles are stored in, and require release from, a source before they can be used effectively. Together, a volatile-containing source and a method for delivering or dispersing the same may be referred to as a system.

Many systems are available in the present market place for dispersing volatiles. These systems include aerosol canisters, gaseous 'bombs', oil heating pots, burning incense, electric or gas heating pads, burning torches, air filter/blowers, oil lamps, and scented candle systems.

Unfortunately, each of the current systems has detriments. As one example, aerosol canisters are a common way to deliver an aromatic or insecticide volatile, but the delivery time period is very short, the delivery range is necessarily narrow, and the volatiles delivered do not remain airborne and almost immediately stick to a surface. Additionally, aerosol canisters require repeated manual application to even attempt a continuous delivery stream of the selected volatile. The need for manual application and reapplication, effectively means that the atmospheric concentrations of volatiles delivered by aerosol canisters follows a sinusoidal curve from a maximum to a minimum.

As a second example, plug-in air fresheners operate as electric heating pads, which warm an adjacent volatile containing source, causing the volatile to disperse. Unfortunately, while this type of system may be used for long-duration volatile delivery, the system is not readily portable, must remain connected to an electrical source, and requires custom-made and non-interchangeable volatile sources. Most commonly, plug-in air fresheners available only for use in small confined spaces immediately adjacent a wall outlet.

As a third example, air filters/blowers operate as to blow air across a volatile or scent containing solid dispersed on a porous filter. Unfortunately, this type of system is similarly tied to an electrical source, is often very expensive, heavy, and requires a constant supply of expensive porous filters.

As a fourth example, scented candle systems contain selected volatiles dispersed in solid wax base material that acts as a source. This base material has a certain transition temperature ($t_g$) at which the solid base material becomes liquid. During use, an operator lights a wick suspended in the solid base material. Heat, as high as 2000 degrees Celsius, immediately surrounds the burning wick, and begins to melt a portion of the base material, turning it into a liquid. As the base material melts, a pool of molten base material is defined from which the selected volatiles are released into the immediate atmosphere. Conventional scented candle systems are easily repositioned at need, are inexpensive, and may be used with commonly available scented candles having a regular shape.

Figure 1:
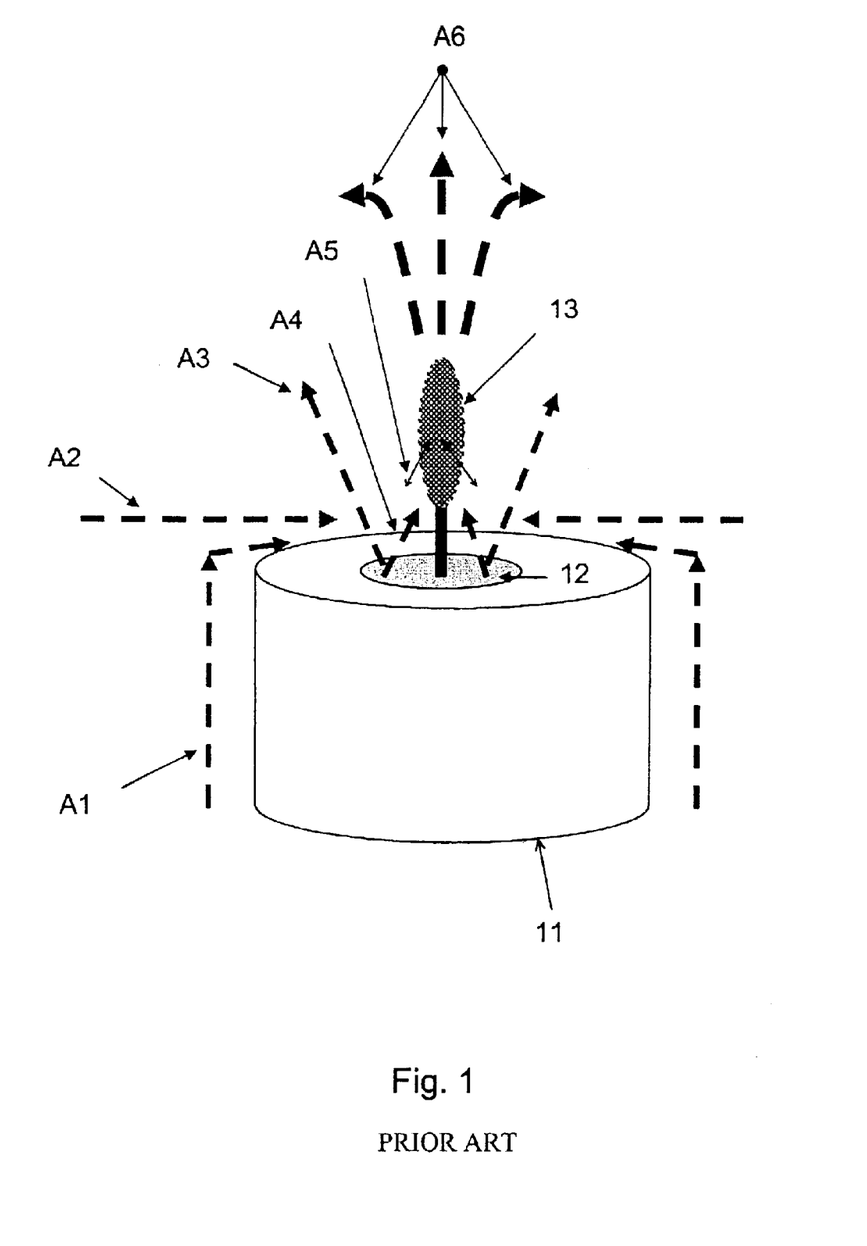
FIG. 1 is a schematic view of air flow around a conventional burning candle.

Referring now to FIG. 1, a burning candle 11 includes a wax pool 12 and a candle flame 13. Candle 11 contains volatiles, which may include fragrances, essential oils, insect repellents, insecticides, and anti-microbial compounds. During use, the strongest outside air flows A1, A2 are drawn into candle flame 13. Candle flame 13, as hot as 2000° C., warms air flows A1, A2 and, in combination with the combined pressure from both air flows A1, A2 creates a broad and strong hot airflow as updraft A6. With these combined pressures, updraft A6 remains hot enough to damage and render ineffective most volatiles within several unit lengths of candle flame 13, as will be explained.

During use, thermal energy A5 radiates from candle flame 13 and creates wax pool 12. A plurality of volatiles volatilize from wax pool 12 along pathways A3, A4, are influenced by outside air flows A1, A2, pass adjacent or through candle flame 13, and are consumed in significant amounts and broken down into smaller non-effective or harmful elements. Only a small portion of volatiles directed along pathway A3 might randomly escape thermal consumption either directly in candle flame 13, or thereafter in updraft A6. Volatiles directed along pathway A4 are completely consumed.

In this conventional system, air flow A2 is just as strong as or stronger than air flow A1. Consequently, when the vector forces of air flows A1 and A2 are combined, an inward pressure vector towards candle flame 13 exists which substantially prevents volatile escape. Furthermore, since the pressure vectors of air flows A1 and A2 exist around the circumference of candle flame 13, a great deal of turbulence exists around candle flame 13 and within updraft A6. This turbulence further minimizes the distribution of any escaped volatiles beyond a narrow range adjacent burning candle 11. In other words, air flows A2, A1 are not efficiently harnessed to aid volatile movement away from candle flame 13 and are not effectively harnessed to distribute any volatiles that survive.

As noted above, conventional candle systems have many disadvantages that result in the unsatisfactory delivery of the volatiles, most commonly selected fragrances or aromas. The principal disadvantages of the presently known candle systems are unregulated volatile distribution and unpredictable volatile combustion, namely that a large percentage of the volatiles pass through the 2000° C. flame and are thermally broken down into smaller molecules and substances. Many of these smaller molecules are either harmful to others or have no fragrance or aroma value. A secondary cause of this unregulated combustion is the formation of irregular molten pools, many of which can only release the volatile compounds immediately adjacent to or directly into the flame, causing an even greater percentage of thermal breakdown.

As a result of the multiple disadvantages inherent with conventional delivery candle systems, manufacturers have been forced to respond by (1) improving the thermal resistance of the active volatiles placed in the base material, (2) (increasing the concentration of volatile components within the base material to an expensive and unnecessarily high level, (3) selecting volatile compounds which have non-harmful combustion components, (4) changing or limiting desirable volatile (fragrance) components requiring while increase in secondary non-desirable and expensive volatile components, (5) changing the wax base material to a more expensive substance, (6) changing the wick material to a more expensive one having a lower temperature of combustion, and (7) placing hoods above the wick in attempts to minimize wick flare-ups and re-radiate heat downward to minimize irregular molten pool shapes.

Unfortunately, available commercial candle based systems are only positioned to protect the candle flame from being blown out or for pleasing decoration or design purposes. Many candle hoods substantially decrease volatile performance because of inadequate design and use.

A candle hood, disclosed in U.S. Pat. No. 6,190,439, is narrower at the top than the bottom and the candle is retained within walls extending above the molten pool level. Consequently, volatiles that escape from the molten pool are forced into a narrow cone containing the hot combustion gasses, and are thermally consumed. Volatiles that do escape the hot combustion gasses experience the additional turbulence resulting from the pressure gradient between the wide bottom and narrow top openings of the hood. U.S. Pat. No. 6,190,439 also teaches a filter at the top of the hood that further limits volatile diffusion, increases volatile combustion risk, and drastically minimizes laminar air flow away from the burning wick by creating a backpressure.

U.S. Pat. No. 6,152,728 discloses a fragrance dispensing candle holder which requires an elaborate, and expensive to produce, annular shoulder portion and holder for a limited candle size. Consequently, this design is not interchangeable with multiple candles from differing manufacturers, is difficult to operate accurately, and does not adequately protect the burning wick from air disturbances.

Aromatic systems, similar to that disclosed in U.S. Pat. No. 6,354,710, are expensive, require electrical power, and operate by warning a base wax. This type of aromatic system requires volatile compounds which are different from those conventionally used in candle systems, require expensive scientific review of each new volatile compounds, cannot be easily transported during use, and further requires a flameless heat source to operate effectively.

The candle holder taught by Lee in U.S. Pat. No. 5,197,454 only diminishes fragrance or volatile performance in a number of ways. A retainer element is required that extends above the molten pool level and prevents the air from picking up the volatiles and transporting them away from the flame before combustion, while at the same time increasing the odds of combusting any volatiles which do escape from the molten pool. The volatile and smoke exit rate is so slow as to prevent almost any real distribution of fragrance within a room. The Lee system further minimizes performance volatile distribution by trapping the volatiles and combustion gasses below a bowl (and cup) thus creating a positive downward pressure and increased turbulence to further minimize volatile distribution.

OBJECTS AND SUMMARY OF THE INVENTION

An object of the present invention is to provide a system or apparatus, and a method for improving the delivery of volatiles from a burning candle, which overcomes the limitations described above.

Another object of the present invention is to provide a method and a system for improving the delivery of volatiles from a candle by improving and regulating a laminar air flow to minimize combustion of volatiles, to create a more voluminous liquid wax pool for release of volatiles, while maintaining or reducing production and fabrication costs.

The present invention relates to a system and a method for improving the delivery of volatiles from a burning candle by providing a stabilized laminar gas flow adjacent a volatile-containing molten pool, ensuring an enlarged molten pool by close regulation of thermal transfer between a monolithic candle mass and the surrounding atmosphere, and minimizing volatile loss through unregulated thermal gradients.

According to one embodiment of the present invention, there is a volatile release system, comprising: a candle on a first surface, the candle having a wick, the candle including a plurality of volatiles disposed within wax, a chimney on the first surface extending equidistant to an outer surface of the candle, the chimney defining a top and a bottom section, the top opening being an unrestricted opening, a plurality of air inlets extending through the chimney, proximate both the first surface and the outer surface of the candle, a top of each the plurality of air inlets being between a top surface of the candle and the first surface, the chimney extending above the top surface of the candle, and an aspect ratio Y, of a height of the chimney to a diameter of the chimney, being $1.0 \leq Y \leq 2.50$, whereby during a use when the wick is lit, a laminar air flow forms proximate the outer surface and draws the volatiles away from the wick and out the top opening.

According to another embodiment of the present invention, there is provided a volatile release system, wherein: a ratio X, of a diameter of the top opening to a diameter of the bottom section is: $60\% \leq X \leq 160\%$.

According to another embodiment of the present invention, there is provided a volatile release system, wherein: the ratio X is: $80\% \leq X \leq 120\%$.

According to another embodiment of the present invention, there is provided a volatile release system, wherein: the ratio X is: $95\% \leq X \leq 105\%$.

According to another embodiment of the present invention, there is provided a volatile release system, wherein: the aspect ratio Y is: $1.0 \leq Y \leq 2.0$.

According to another embodiment of the present invention, there is provided a volatile release system, wherein: the aspect ratio Y is: $1.2 \leq Y \leq 1.8$.

According to another embodiment of the present invention, there is provided a method for releasing a volatile, comprising the steps of: providing a candle on a first surface, the candle having a wick, the candle including a plurality of volatiles disposed within wax, lighting the wick, and providing a chimney on the first surface equidistant to an outer surface of the candle, the chimney comprising: a top opening and a bottom section on the chimney, a plurality of air inlets extending through the chimney proximate both the first surface and the outer surface of the candle, a top of each the plurality of air inlets being between a top surface of the candle and the first surface, the chimney extending above the top surface of the candle, and an aspect ratio Y, of a height of the chimney to a diameter of the chimney, being $1.0 \leq Y \leq 2.50$, whereby after the steps of lighting the wick and providing the chimney, a laminar air flow forms proximate the outer surface and draws the volatiles away from the wick and out the top opening.

According to another embodiment of the present invention, there is provided a volatile release system, comprising: a candle on a first surface of a base plate, the candle having a wick, the candle including a plurality of volatiles disposed within wax, the base plate including a plurality of air inlets on an outer surface, a chimney extending away from the first surface, equidistant to an outer surface of the candle, the chimney defining a top and a bottom opening, the top opening being an unrestricted opening, the plurality of air inlets extending through the base plate to a respective plurality of inner openings on the first surface proximate the outer surface of the candle, and an aspect ratio Y, of a height of the chimney to a diameter of the chimney, being $1.0 \leq Y \leq 2.50$, whereby during a use when the wick is lit, a laminar air flow forms proximate the outer surface and draws the volatiles away from the wick and out the top opening.

According to another embodiment of the present invention, there is provided a volatile release system, wherein: respective pluralities of the air inlets and the inner openings define a plurality of closed pathways in communication between the first surface adjacent the outer surface of the candle, and an outer edge surface of the base plate.

According to another embodiment of the present invention, there is provided a volatile release system, further comprising: a recess on the first surface, and the recess effective to receive an edge of the bottom opening of the chimney, whereby the recess prevents a movement of the chimney relative to the base plate during the use.

According to another embodiment of the present invention, there is provided a volatile release system, wherein: respective pluralities of the air inlets and the inner openings define respective open channels between the first surface adjacent the outer surface of the candle, and an outer edge surface of the base plate.

According to another embodiment of the present invention, there is provided a method for releasing a volatile, comprising the steps of: providing an candle on a first surface of a base plate, the candle having a wick, the candle including a plurality of volatiles disposed within wax, the base plate including a plurality of air inlets on an outer surface, the plurality of air inlets extending through the base plate to a respective plurality of inner openings on the first surface proximate an outer surface of the candle, lighting the wick, and providing a chimney extending away from the first surface and equidistant to the outer surface of the candle, the chimney comprising: a top and bottom opening on the chimney, the top opening being an unrestricted opening, the chimney extending above a top surface of the candle, and an aspect ratio Y, of a height of the chimney to a diameter of the chimney, being $1.0 \leq Y \leq 2.5$, whereby after the steps of lighting the wick and providing the chimney, a laminar air flow forms proximate the outer surface and draws the volatiles away from the wick and out the top opening.

According to another embodiment of the present invention, there is provided a method for releasing a volatile, wherein: in the step of providing a candle on a first surface of a base plate, respective pluralities of the air inlets and the inner openings define a plurality of closed pathways in communication between the first surface adjacent the outer surface of the candle, and an outer edge surface of the base plate.

According to another embodiment of the present invention, there is provided a method for releasing a volatile, wherein: in the step of providing a candle on a first surface of a base plate, respective pluralities of the air inlets and the inner openings define respective open channels between the first surface adjacent the outer surface of the candle, and an outer edge surface of the base plate.

The above, and other objects, features and advantages of the present invention will become apparent from the following description read in conduction with the accompanying drawings, in which like reference numerals designate the same elements.

DETAILED DESCRIPTION OF THE PREFERRED EMBODIMENTS

Figure 2:
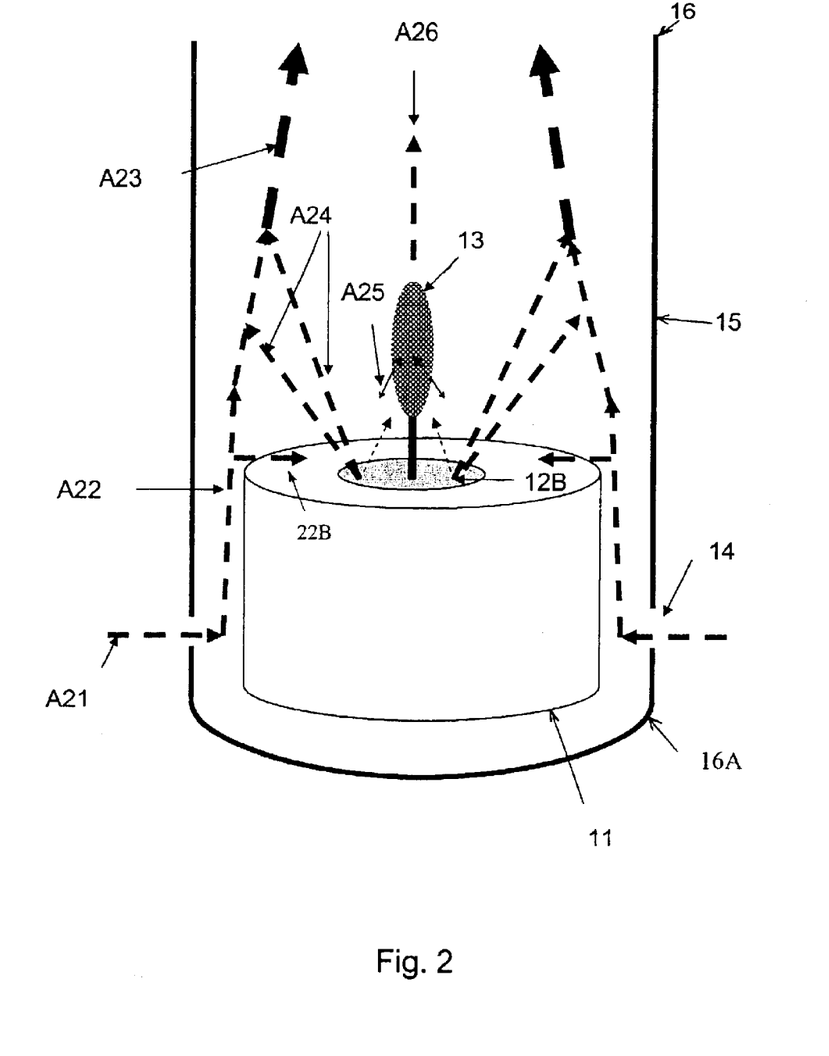
FIG. 2 is another schematic view of air flow around a burning candle and a chimney according to one embodiment of the present invention.

Referring now to FIG. 2, a tube 15 includes a plurality of inlets 14 positioned about an outer circumference having a top opening 16 and a bottom opening 16A. Tube 15 surrounds candle 11, candle flame 13, and a larger sized wax pool 12B, as will be explained. Top opening 16 and bottom opening 16A are aligned vertically and walls of tube 15, joining top opening 16, inlets 14, and bottom opening 16A, are smooth and either in parallel or positioned in a generally outward-opening cone-shape. Inlets 14 are below a top surface of candle 11. Inlets 14 are sized to supply all the air necessary to exceed the normal combustion requirements for candle flame 13.

It is to be understood, that opening 16 may be greater in diameter than opening 16A by up to about 20%, but thereafter the effectiveness of the present system decreases and outside turbulence detrimentally effects the system, as will be explained. It is to be further understood, that walls of tube 15 have a length at least twice the distance between a top of inlets 14 and the top of candle 11.

During use, the design of the present invention provides much larger amounts of active volatiles into the air and a greatly reduced rate volatile destruction by critically supplying and redirecting the air flow adjacent to wax pool 12B and candle flame 13.

During use, pluralities of fresh air flow A21 passes through respective inlets 14, confronts candle 11, and is redirected solely into vertical updrafts A22, in the form of a laminar tube surrounding sides of candle 11. As updrafts A22 rise, they gain kinetic energy and uninterrupted momentum by passing between sides of candle 11 and walls of chimney 15. In this condition, updrafts A22 form a substantially laminar flow path, undisturbed by outside pressure. Simultaneously, a hot air flow A26 rises directly from candle flame 13, and undisturbed by non-parallel/non-laminar air currents, passes vertically through opening 16. Undisturbed candle flame 13 further produces an undisturbed and uniform radiant energy A25 downward toward candle 11 and creates a larger and uniform wax pool 12B. Consequently, wax pool 12B is volumetrically much larger than conventional wax pools and releases a greater volume of active volatiles A24.

As updrafts A22 reach the top of candle 11 no and even negative pressure drops occur, and consequently only minor and random inward air flows 22B exist, as shown. The majority of updrafts A22 continue to rise vertically and as a result updrafts A22 draw active volatiles A24 away from candle flame 13 and incorporate them into a broad updraft A23. Broad updraft A23 includes fresh updraft A22, active volatiles A24 and, gaining velocity and momentum, becomes stronger as it rises.

Due to wide opening 16, broad updraft A23 quickly disperses from the system and avoids being drawn downward. A narrow opening at the top of chimney 15 would cause broad updraft A23 to turn back upon itself, join hot air flow A26, and either immediately consume active volatiles A24 or turn them downward into candle flame 13 for thermal consumption and generation of other undesirable or harmful volatiles. Further, use of retainer elements that block the top of candle 11, would increase inward pressure drop and consumption of volatiles A24 in wax pool 12B.

Figure 3:
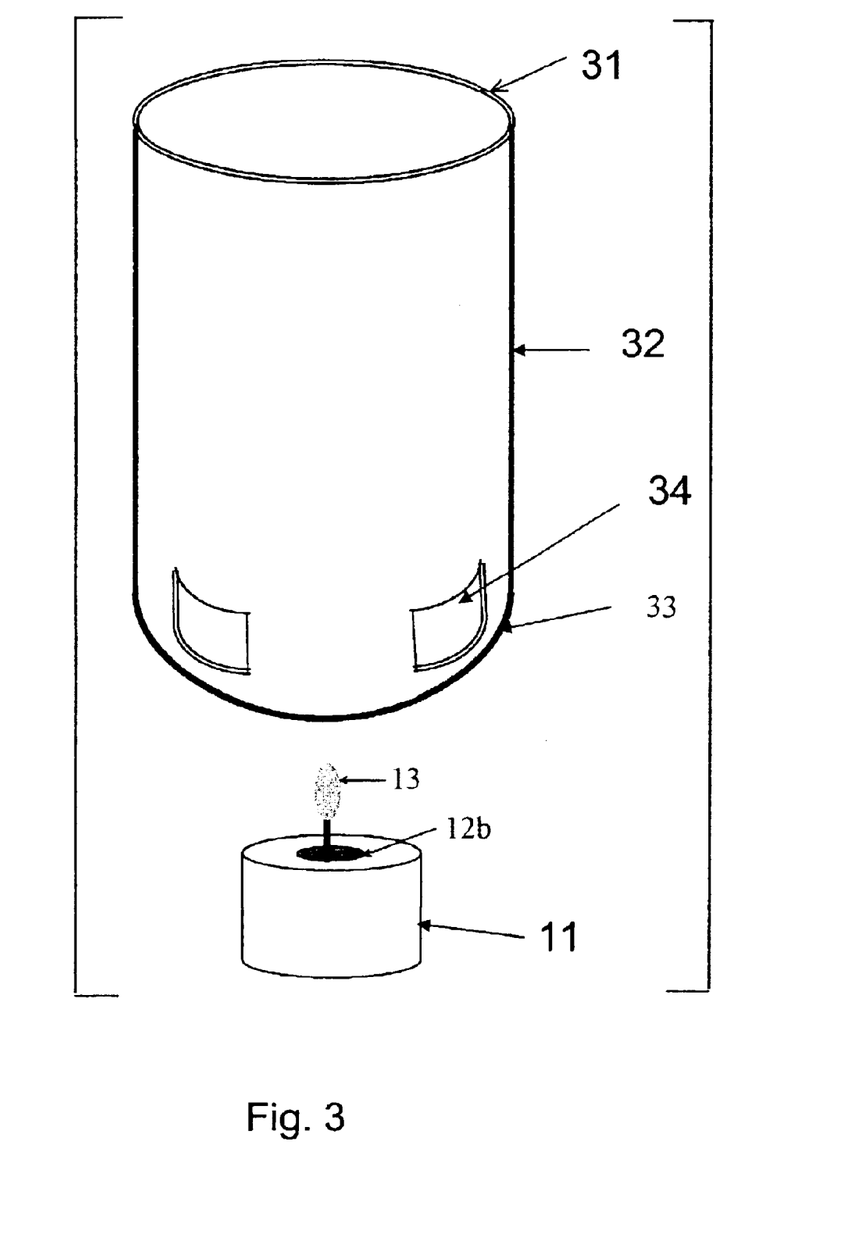
FIG. 3 is an exploded view of one embodiment of the present invention.

Referring now to FIG. 3, one embodiment of the present invention includes a tube 32 defining a top opening 31 and a bottom opening 33. A plurality of inlets 34 is spaced around an outer circumference of tube 32 at a height adjacent to the outer circumference of scented candle 11, and below a top surface of candle 11 after an assembly. The inner walls of tube 32 are not interrupted in any manner other than by inlets 34 thereby limiting sources for turbulence origination.

During use, candle flame 13 is ignited and tube 32 is centered and placed over candle 11 on a flat surface (not shown). As a broad and stable wax pool 12B forms, fresh air enters inlets 34, meets walls of candle 11, and is redirected upward as a laminar tube surrounding the outer circumference of candle 11. As fresh air rises smoothly along walls of tube 32 volatiles (not shown) are drawn outward from wax pool 12B, preventing their destruction in candle flame 13 or recapture in downdrafts. Consequently, volatiles within the fresh air easily escape top opening 31, which increase the viable volatiles available for use.

Figure 4:
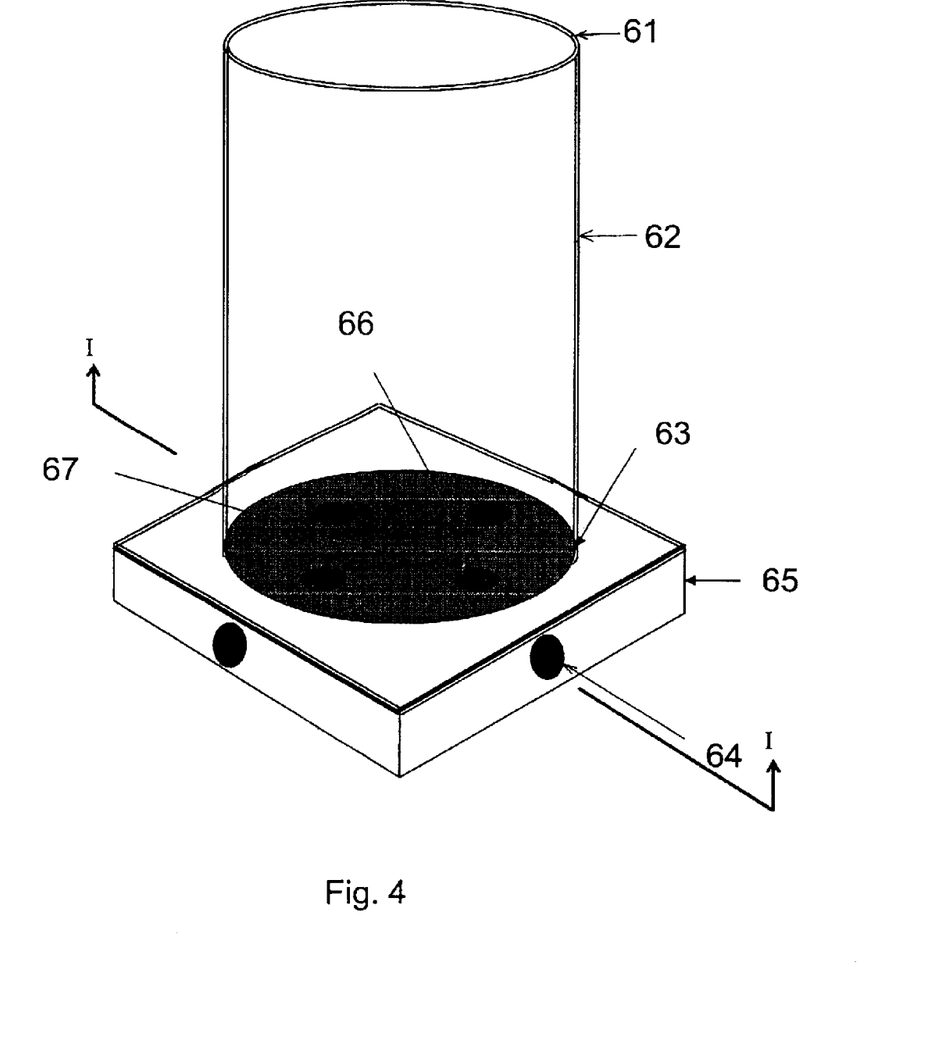
FIG. 4 is a perspective view of a second embodiment of the present invention.
Figure 5:
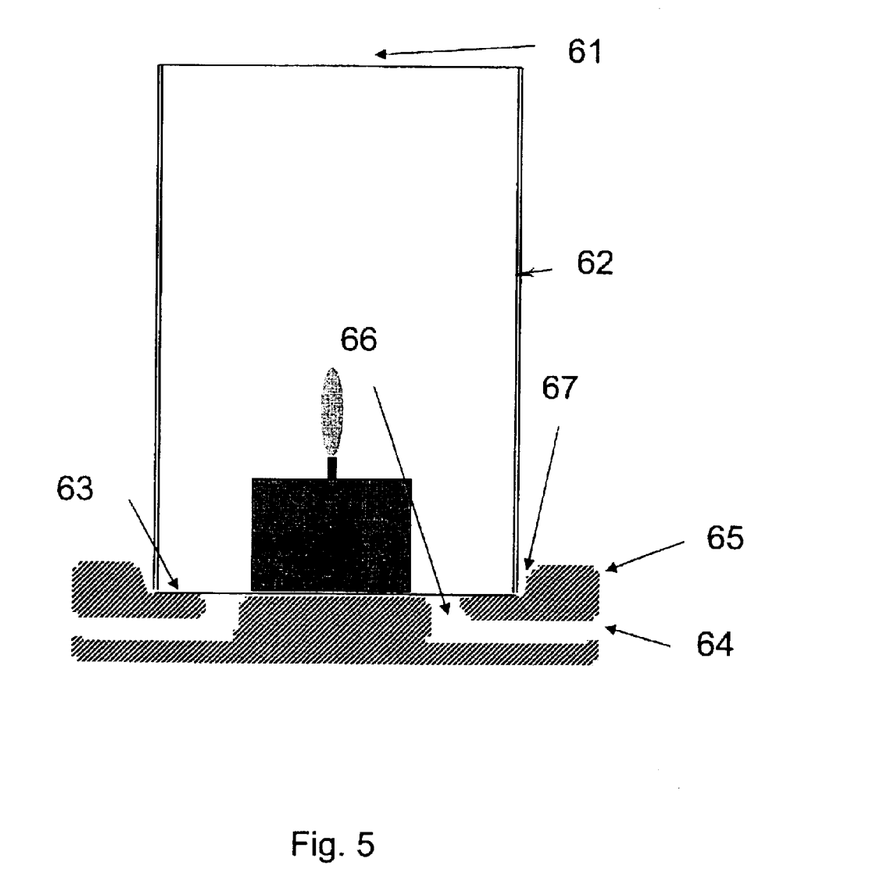
FIG. 5 is a cross sectional view along lines I–I in FIG. 4.
Figure 6:
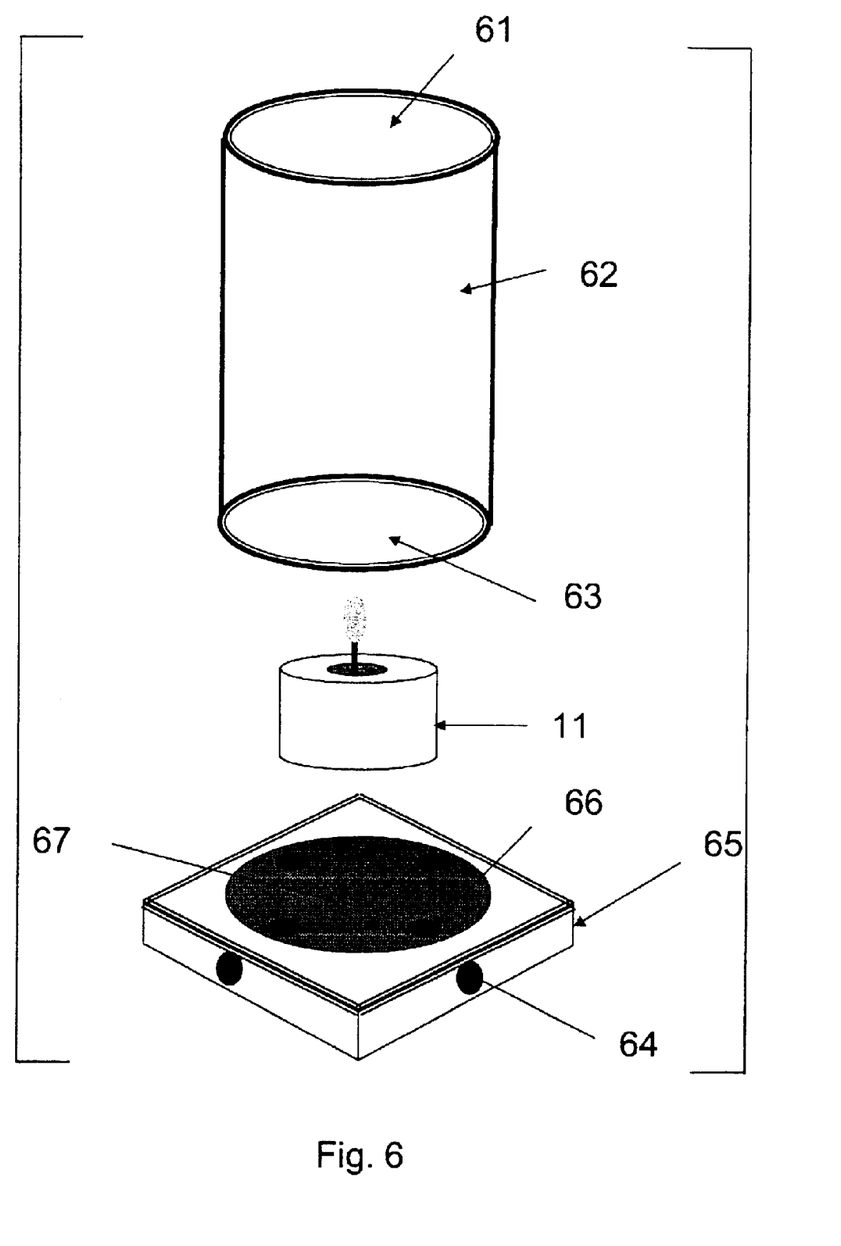
FIG. 6 is an exploded view of the second embodiment of the present invention.

Referring now to FIGS. 4 through 6, an alternative embodiment to the present invention includes a tube 62 and a tube base 65. Tube 62 includes a wide top opening 61 and an equally wide bottom opening 63. Base 65 includes a centrally located recess 67 having a shape similar to the outer circumference of tube 62. During an assembly, tube 62 is placed in recess 67 and walls of recess 67 (shown, but not described) prevent tube 62 from moving sideways relative to base 65. In this manner base 65 firmly supports tube 62.

Base 65 includes a plurality of inlet tunnels 64 allowing fresh air to enter from respective outer surfaces of base 65 to respective inner openings 66, each adjacent walls of scented candle 11. Inner openings 66 are located proximate an outer circumference of candle 11.

During use, candle 11 is lit and centered on base 65. Tube 62 is lowered over scented candle 11 and positioned within recess 67. Next, fresh air enters inlet tunnels 64 and, in passage, is redirected in to a vertical flow exiting inner openings 66. Upon exiting inner openings 66, the fresh air flow forms a laminar tube surrounding candle 11 rising uniformly along the outer circumference of candle 11. As a consequence of this design, fresh air rises smoothly along walls of tube 62 past stable wax pool 12B and, due to the resultant lower pressure gradient at the top of candle 11, volatiles (not shown) are drawn outward from wax pool 12B, preventing their destruction in candle flame 13 and recapture in downdrafts. Consequently, volatiles within the fresh air easily escape top opening 31, and increase the allowable volatiles available for use.

Figure 7:
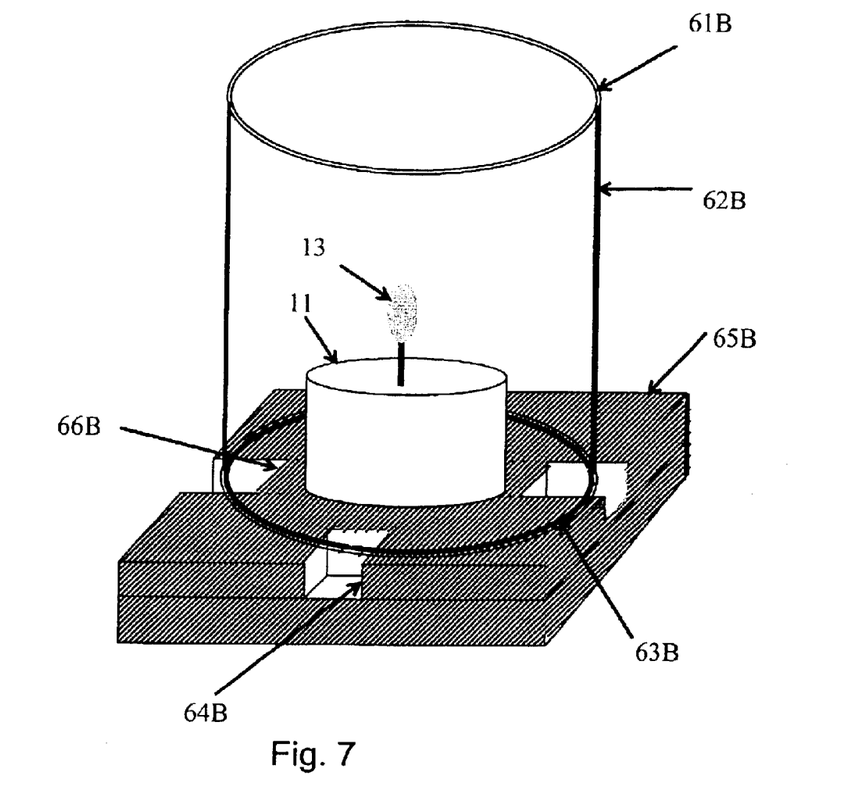
FIG. 7 is a perspective view of a third embodiment of the present invention.
Figure 8:
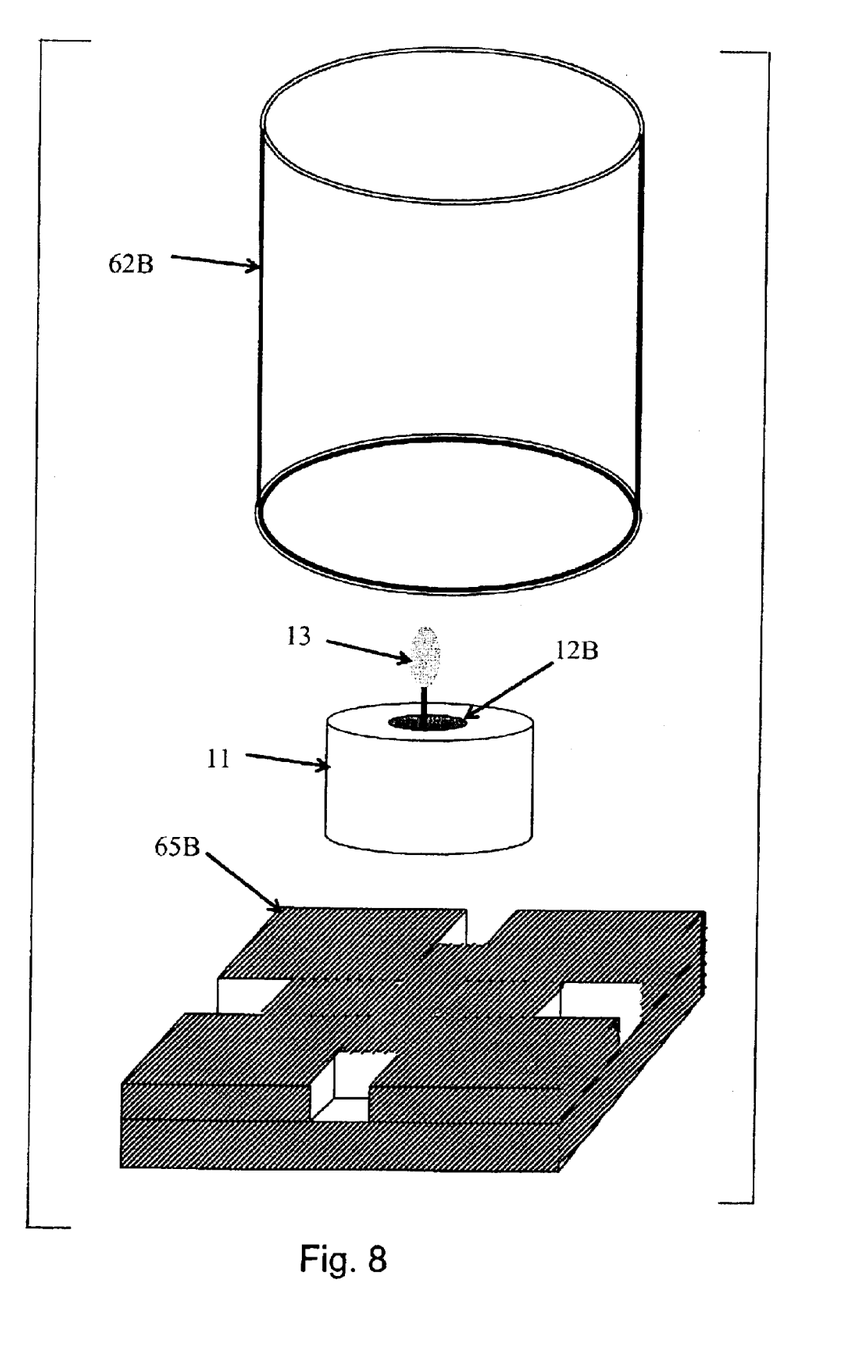
FIG. 8 is an exploded side view of the third embodiment of the present invention.

Referring now to FIGS. 7 and 8, an alternative embodiment of the present invention includes a tube 62B and a base 65B. Tube 62B includes a wide top opening 61 and an equally wide bottom opening 63B. Base 65B provides a firm and flat surface to support bottom opening 63B.

Base 65B includes a plurality of inner openings 66B allowing fresh air to enter from respective inlet openings 64B, on outer areas of base 65B, and pass under bottom opening 63B. Inner openings 66B and inlet openings 64B are parts of respective channels formed in base 65B. Each inner opening 66B is adjacent respective inner walls of tube 62B and an outer circumference of candle 11. For manufacturing convenience, the present embodiment positions inner openings 66B proximate the walls of tube 62B, thus eliminating the need to form openings in tube 62B and reducing manufacturing costs.

In this embodiment, inner openings 66B extend more than one-half of the distance between the outer circumference of candle 11 and the inner wall of tube 62B. Consequently, inner openings 66B are effective to provide fresh air in a laminar tube rising around the outer circumference of candle 11 and transporting any volatiles released during use safely away from candle flame 13.

In combination, the above embodiments provide substantial benefits over conventional designs. Namely, the above embodiments allow the use of conventional scented (volatile) candles, which eliminates any need to reformulate the candle/volatile compositions and eliminates any additional research and development costs. Further, the above embodiments allow more effective distribution of volatiles during use over a conventional scented candle used alone, while maintaining easy repositioning of the system without a need for electrical fans or expensive filters. Finally, since the present design allows greater volatile economy per use, manufacturers may lower the required additive percentage of volatiles per candle, further reducing manufacturing costs.

EXPERIMENTS 1

Commercial candles (Glade, strawberry-cream-scent, SC Johnson & Sons., Inc. Racine, Wis.) were purchased and trained panelists evaluated the volatile (fragrance) performance and an expert perfumer gave volatile (fragrance) descriptions. In this experiment, the scent is the volatile.

Two types of one-piece tubes (chimneys) were used in the evaluation test. Tube A had a height of 15 cm, an open bottom diameter of 11 cm, an open top diameter of 7 cm, and no inlet. Tube B had a height of 15 cm, an open bottom diameter of 11 cm, an open top diameter of 7 cm, and four (4) inlets equally positioned around a bottom diameter adjacent a candle. Tube C had a height of 20 cm, an open bottom diameter of 9 cm, a narrow open top diameter of 2 cm, and four (4) inlets equally positioned around a bottom diameter adjacent a candle. The respective tube aspect ratios (height/bottom diameter) are: Tube A (15 cm/11 cm)=1.36, Tube B (15 cm/11 cm)=1.36, Tube C (20 cm/9 cm)=2.22. The results are shown below in Table I:

TABLE I

| Tube/Chimney type | Time (hrs) | Temperature at top opening | Wax Pool Size (DIA in mm) | Description of volatile |
| --- | --- | --- | --- | --- |
| No Chimney | 2 | Warm | 35 | Very weak odor |
| Type A (no inlet) | 2 | Warmer | 50 | Very weak and inconsistent odor |
| Type B | 2 | Comfortably Warm | 55 | Strong, natural, pleasant, well balance odor |
| Type C | 2 | Uncomfortably Warm | 60 | No distinctive odor |

EXPERIMENT 2

Again, commercial candles (Glade, berry-scent, SC Johnson & Sons., Inc. Racine, Wis.)) were purchased and trained panelists evaluated the volatile (fragrance) performance and an expert perfumer gave volatile (fragrance) descriptions. In this experiment, the scent is the volatile.

Three types of tubes were used as chimneys in conjunction with a base formed as base 65B. Tube type D was 16 cm in height and 10 cm in diameter. Tube type E was 23 cm in height and 10 cm in diameter. Tube type F was 19 cm in height and 13 cm in diameter. Each of the tubes was made of quartz (Pyrex). A measure of the air flow rate in each test was performed using a commercial smoke device positioned adjacent inlet passages 64B, and qualitative measurements were taken. The respective tube aspect ratios (height/bottom diameter) are: Tube D (16 cm/10 cm)=1.60, Tube E (23 cm/10 cm)=2.30, Tube F (19 cm/13 cm)=1.46. The results are shown below in Table II:

TABLE II

| Type of tube/chimney | Smoke | Performance |
| --- | --- | --- |
| Without Chimney | Randomly distributed around burning candle | Poor with weak odor |
| Type D | Very fast updraft and smoke exited along wall of tube | Fair with remarkable odor |
| Type E | Fast updraft and little smoke existed around candle | Good with remarkable and distinctive odor |
| Type F | Moderately fast updraft and a moderate amount of smoke went out by candle. | Excellent with warm and well balanced berry odor. |

After review of both Experiment I and Experiment II it is generally apparent: (1) that fresh air inlets are mandatory for any performance increase, (2) that laminar-type air flow to pull volatiles away from the wax pool is required for performance increase or economic benefits, (3) that there should be no barrier immediately adjacent the top surface of the candle in order to minimize back pressure into the flame, (4) that where the up draft is very fast, mixing between volatiles and fresh air is poor, and consequently only a limited quantity of volatiles is properly distributed, (5) that where the updraft is very slow there is little volatile distribution and greater combustion and loss of volatiles, (6) that where an aspect ratio of a chimney (height/diameter) is between about 1.00 and 2.50 there is an improved opportunity for improved volatile distribution depending upon other related factors including candle height, (7) that a ratio of a tubes top to bottom diameters is between about 60% to 160% to promote unrestricted smooth laminar air flow, and (8) that where the updraft is moderate, both volatile mixing with fresh air is superior and volatile distribution is superior. Finally, it is also clear that rapid exit of the moderately mixed fresh air and volatiles from the tube and candle flame is required to minimize any remixing, volatile degradation, additional turbulence, and maximize volatile performance at low cost.

It should be understood by those skilled in the art that, as noted hereinabove and as used in the claims, the phrase volatile(s) refers interchangeably to a variety of fragrances, aromas, essential oils, pesticides, insecticides, pest-repellents, and anti-microbial compounds.

It should also be understood by those skilled in the art that while tubes (chimneys) and candles may have different shapes from cylindrical to angular, positioning the tube centered on or equidistant to the candle allows for the smoothest airflow around the sides of the candle.

Although only a single or few exemplary embodiments of this invention have been described in detail above, those skilled in the art will readily appreciate that many modifications are possible in the exemplary embodiment(s) without materially departing from the novel teachings and advantages of this invention. Accordingly, all such modifications are intended to be included within the spirit and scope of this invention as defined in the following claims.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A volatile release system, comprising:

a candle on a first surface;

said candle having a wick;

said candle including a plurality of volatiles disposed within wax;

a chimney on said first surface extending equidistant to an outer surface of said candle;

said chimney defining a top and a bottom section;

said top opening being an unrestricted opening;

a plurality of air inlets extending through said chimney, proximate both said first surface and said outer surface of said candle;

a top of each said plurality of air inlets being between a top surface of said candle and said first surface;

said chimney extending above said top surface of said candle; and an aspect ratio Y, of a height of said chimney to a diameter of said chimney, being $1.0 \leq Y \leq 2.50$, whereby during a use when said wick is lit, a laminar air flow forms proximate said outer surface and draws said volatiles away from said wick and out said top opening.

2. A volatile release system, according to claim 1, wherein:
a ratio X, of a diameter of said top opening to a diameter of said bottom section is: 60%≦X≈160%.

3. A volatile release system, according to claim 2, wherein:
said ratio X is: 80%≦X≦120%.

4. A volatile release system, according to claim 3, wherein:
said ratio X is: 95%≦X≦105%.

5. A volatile release system, according to claim 1, wherein:
said aspect ratio Y is: 1.0≦Y≦2.0.

6. A volatile release system, according to claim 5, wherein:
said aspect ratio Y is: 1.2≦Y≦1.8.

7. A method for releasing a volatile, comprising the steps of:
providing a candle on a first surface;
said candle having a wick;
said candle including a plurality of volatiles disposed within wax;
lighting said wick; and
providing a chimney on said first surface equidistant to an outer surface of said candle, said chimney comprising:
a top opening and a bottom section on said chimney;
a plurality of air inlets extending through said chimney proximate both said first surface and said outer surface of said candle;
a top of each said plurality of air inlets being between a top surface of said candle and said first surface;
said chimney extending above said top surface of said candle; and
an aspect ratio Y, of a height of said chimney to a diameter of said chimney, being 1.0≦Y≦2.50, whereby after said steps of lighting said wick and providing said chimney, a laminar air flow forms proximate said outer surface and draws said volatiles away from said wick and out said top opening.

8. A volatile release system, comprising
a candle on a first surface of a base plate;
said candle having a wick;
said candle including a plurality of volatiles disposed within wax;
said base plate including a plurality of air inlets on an outer surface;
a chimney extending away from said first surface, equidistant to an outer surface of said candle;
said chimney defining a top and a bottom opening;
said top opening being an unrestricted opening;
said plurality of air inlets extending through said base plate to a respective plurality of inner openings on said first surface proximate said outer surface of said candle; and
an aspect ratio Y, of a height of said chimney to a diameter of said chimney, being 1.0≦Y≦2.50, whereby during a use when said wick is lit, a laminar air flow forms proximate said outer surface and draws said volatiles away from said wick and out said top opening.

9. A volatile release system, according to claim 8 wherein:
a ratio X, of a diameter of said top opening to a diameter of said bottom opening is: 60%≦X≦160%.

10. A volatile release system, according to claim 9, wherein:
said ratio X is: 80%≦X≦120%.

11. A volatile release system, according to claim 10, wherein:
said ratio X is: 95%≦X≦105%.

12. A volatile release system, according to claim 8, wherein:
respective pluralities of said air inlets and said inner openings define a plurality of closed pathways in communication between said first surface adjacent said outer surface of said candle, and an outer edge surface of said base plate.

13. A volatile release system, according to claim 12, further comprising:
a recess on said first surface; and
said recess effective to receive an edge of said bottom opening of said chimney, whereby said recess prevents a movement of said chimney relative to said base plate during said use.

14. A volatile release system, according to claim 8, wherein:
respective pluralities of said air inlets and said inner openings define respective open channels between said first surface adjacent said outer surface of said candle, and an outer edge surface of said base plate.

15. A volatile release system, according to claim 8, wherein:
said aspect ratio Y is: 1.0≦Y≦2.0.

16. A volatile release system, according to claim 15, wherein:
said aspect ratio Y is: 1.2≦Y≦1.8.

17. A method for releasing a volatile, comprising the steps of:
providing an candle on a first surface of a base plate,
said candle having a wick;
said candle including a plurality of volatiles disposed within wax;
said base plate including a plurality of air inlets on an outer surface;
said plurality of air inlets extending through said base plate to a respective plurality of inner openings on said first surface proximate an outer surface of said candle;
lighting said wick; and
providing a chimney extending away from said first surface and equidistant to said outer surface of said candle, said chimney comprising:
a top and bottom opening on said chimney;
said top opening being an unrestricted opening;
said chimney extending above a top surface of said candle; and
an aspect ratio Y, of a height of said chimney to a diameter of said chimney, being 1.0≦Y≦2.5, whereby after said steps of lighting said wick and providing said chimney, a laminar air flow forms proximate said outer surface and draws said volatiles away from said wick and out said top opening.

18. A method for releasing a volatile, according to claim 17, wherein: in said step of providing a candle on a first surface of a base plate, respective pluralities of said air inlets and said inner openings define a plurality of closed pathways in communication between said first surface adjacent said outer surface of said candle, and an outer edge surface of said base plate.

19. A method for releasing a volatile, according to claim 18, wherein: in said step of providing a candle on a first surface of a base plate, respective pluralities of said air inlets and said inner openings define respective open channels between said first surface adjacent said outer surface of said candle, and an outer edge surface of said base plate.

* * * * *